United States Patent
Gupte et al.

(10) Patent No.: US 9,662,286 B2
(45) Date of Patent: May 30, 2017

(54) COMPOSITION OF MENTHOL AND MENTHYL LACTATE, ITS PREPARATION AND ITS USE AS A COOLING, FLAVOURING AND/OR FRAGRANCE AGENT

(71) Applicant: BASF SE, Ludwigshafen (DE)

(72) Inventors: Nitin Gupte, Thane (IN); Avinash Salaskar, Kankavli Sindhudurg (IN); Parag Kulkarni, Mumbai (IN)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/647,532

(22) PCT Filed: Nov. 26, 2013

(86) PCT No.: PCT/EP2013/074694
§ 371 (c)(1),
(2) Date: May 27, 2015

(87) PCT Pub. No.: WO2014/082984
PCT Pub. Date: Jun. 5, 2014

(65) Prior Publication Data
US 2015/0313817 A1   Nov. 5, 2015

Related U.S. Application Data

(60) Provisional application No. 61/730,065, filed on Nov. 27, 2012.

(30) Foreign Application Priority Data

Nov. 27, 2012 (EP) .................................... 12194341

(51) Int. Cl.
C07C 67/08 (2006.01)
C07C 67/31 (2006.01)
(Continued)

(52) U.S. Cl.
CPC ................ *A61K 8/37* (2013.01); *A23L 27/10* (2016.08); *A61K 8/34* (2013.01); *A61Q 5/02* (2013.01);
(Continued)

(58) Field of Classification Search
CPC ......... C07C 69/68; C07C 67/08; C07C 67/31; C07C 67/62; C07C 67/30;
(Continued)

(56) References Cited

U.S. PATENT DOCUMENTS 4,136,163 A   1/1979 Watson et al.
5,783,725 A   7/1998 Kuhn et al.
(Continued)

FOREIGN PATENT DOCUMENTS

JP   H10231238 A   9/1998
WO   WO-2004/037764 A1   5/2004
WO   WO-2007/044146 A1   4/2007

OTHER PUBLICATIONS

Purdue (3 pg. pdf of https://www.chem.purdue.edu/gchelp/liquids/boil.html, downloaded on Aug. 18, 2016).*
(Continued)

*Primary Examiner* — Jafar Parsa
*Assistant Examiner* — Amy C Bonaparte
(74) *Attorney, Agent, or Firm* — Drinker Biddle & Reath LLP

(57) ABSTRACT

The present invention relates to a method of preparing liquid compositions essentially consisting of menthol and menthyl lactate and the use of such compositions as a cooling agent, flavoring agent and/or fragrance agent, products containing such compositions and methods of providing a physiological cooling effect by applying such compositions.

14 Claims, 1 Drawing Sheet

(51) Int. Cl.
  *C07C 67/62* (2006.01)
  *A61K 8/37* (2006.01)
  *A61Q 5/02* (2006.01)
  *A61K 8/34* (2006.01)
  *A23L 27/10* (2016.01)
  *A61Q 11/00* (2006.01)
  *A61Q 19/10* (2006.01)

(52) U.S. Cl.
  CPC .............. *A61Q 11/00* (2013.01); *A61Q 19/10* (2013.01); *C07C 67/08* (2013.01); *C07C 67/31* (2013.01); *C07C 67/62* (2013.01); *A61K 2800/244* (2013.01); *A61K 2800/805* (2013.01)

(58) Field of Classification Search
  CPC ........ A61K 2800/244; A61K 2800/805; A61K 8/34; A61K 8/37; A61Q 5/02; A23L 1/221; A23L 27/10
  USPC .............................. 510/106, 158, 546; 560/4
  See application file for complete search history.

(56) References Cited

U.S. PATENT DOCUMENTS

| | | |
|---|---|---|
| 7,173,146 B1* | 2/2007 | Erman .................... C07C 67/08 560/188 |
| 7,189,760 B2 | 3/2007 | Erman et al. |
| 2004/0018954 A1 | 1/2004 | Su et al. |

OTHER PUBLICATIONS

International Search Report for PCT/EP2013/074694 mailed Feb. 7, 2014.

* cited by examiner

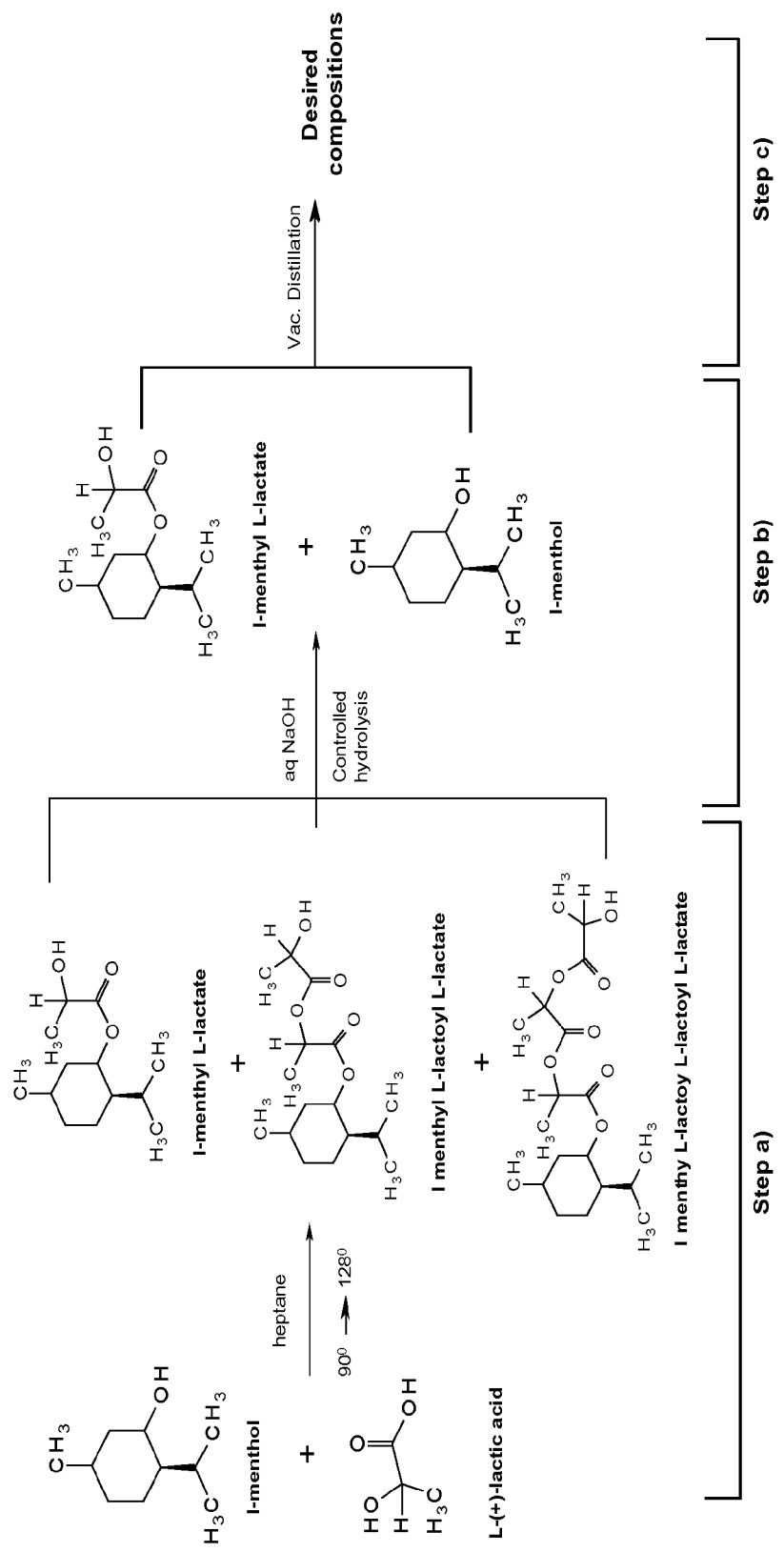

COMPOSITION OF MENTHOL AND MENTHYL LACTATE, ITS PREPARATION AND ITS USE AS A COOLING, FLAVOURING AND/OR FRAGRANCE AGENT

CROSS-REFERENCE TO RELATED APPLICATIONS

This application is a national stage application (under 35 U.S.C. §371) of PCT/EP2013/074694, filed Nov. 26, 2013, which claims benefit of European Application No. 12194341.9, filed Nov. 27, 2012, and U.S. Application No. 61/730,065, filed Nov. 27, 2012, all of which are incorporated herein by reference in their entireties.

The present invention relates to a method of preparing liquid compositions essentially consisting of menthol and menthyl lactate and the use of such compositions as a cooling agent, flavouring agent and/or fragrance agent, products containing such compositions and methods of providing a physiological cooling effect by applying such compositions.

BACKGROUND OF THE INVENTION

Physiological cooling agents are constantly gaining ground in various consumer applications due to their ability of improving desirable sensate properties of the product. These sensate properties are generally explained by the chemical action of these compounds on nerve endings responsible for sensation of cold. Common applications and uses of these compounds include foods, beverages, dentifrices, mouthwashes, toiletries, lotions, confectionery, and pharmaceutical products.

Being a major constituent of peppermint oil, menthol has been used in several of the above mentioned applications for a very long time. Menthol is a physiological cooling agent and is well known for its analgesic, freshening and flavouring effects on the skin and/or the mucous membranes of the mouth. A strong initial cooling sensation can be achieved if the products containing menthol are applied to the skin and/or mucous membrane. However, very often there is a need for products containing a coolant composition in order to provide a long lasting cooling sensation.

Menthyl lactate is also an important ingredient that is valued for its cooling properties. Compared to menthol, menthyl lactate has the advantages of low irritation, long lasting cooling effect and low volatility. Nevertheless menthyl lactate does not produce an initial cooling effect as strong as menthol and therefore its use has been limited to some extent, especially for oral care and skin care products, where the user desires to experience a strong cooling effect as soon as the product is applied. A need therefore was felt for a composition which will contribute the long lasting cooling sensation to a product without the unwanted harshness and unpleasant odor that come from menthol. Various cooling agents have been tried independently or in combination with another agent. The search for more and more cooling and flavouring agents is going on; see WO 00/142983, JP 0632528, JP 10231238, WO 2004/1037764.

Currently, compositions of menthol and menthyl lactate used in the market are prepared by physical mixing of the two components in the required ratio (hereafter called "Artificial Mixture"). The disadvantage thereof is that the menthol and menthyl lactate have to be either melted first at a temperature of 50-60° C. or dissolved in perfume oils, cosmetic oils or glycol solvents such as 1,2-propylene glycol. Furthermore, menthol being slightly volatile, evaporates and generates a strong minty odor which causes unfavorable health and safety issues besides the loss of menthol. Menthyl lactate is available from Symrise GmbH (Germany) in two forms: a crystalline and a non-crystalline form. Each of these solids has the disadvantage of being used in solid form. In case of a non crystalline solid, its container has to be heated in order to transfer the solid from the container whereas in a crystalline solid the presence of 0.1% sodium bicarbonate may cause compatibility problems in the formulation and may need to be removed.

This shows that menthol and menthyl lactate, if added separately in their respective normal solid form to the formulation, are not convenient. This is not favorable for large scale industrial manufacturing processes. On the one hand, such heating process needs to have specific equipment and heating facilities to melt the menthol and menthyl lactate. On the other hand, menthol and menthyl lactate, if added separately in their solid form, are not suitable for cold processing technologies which are a growing trend in the manufacturing in order to save energy and improve productivity. Furthermore, when heated up, menthol being low melting evaporates and generates a strong minty odor that is disagreeable and causes unfavorable health issues, besides the loss of menthol.

The problem to be solved by the invention is the provision of a composition of menthol and menthyl lactate which is liquid at room temperature and whose crystallization point is much below room temperature. Such a composition could be added directly in liquid form into a desired formulation which makes the formulation process more convenient without raising any health and safety issues.

There are reports in the technical literature where menthol and menthyl lactate have been used in the same formulation by adding menthol and menthyl lactate separately and there is no mention about eutectic mixture formation in this formulation.

US 2004/10018954 describes compositions containing menthol and menthyl lactate in different proportions in the range of 1:4 to 4:1 and its effect on the freezing point of the mixture. It states that menthol and menthyl lactate can be physically mixed in different ratios and stirred for 20 minutes to get a clear liquid having a crystallization point below room temperature. But it was observed that it is very difficult to stir two solids and it also takes a long time (sometimes even 24 hours) to obtain a clear liquid.

WO2007/044146 describes a method for producing menthyl lactate from menthol and lactic acid. The method disclosed therein aims at as high as possible yields of ML. Maximizing the overall yield of ML is emphasized in the summary section of said description. The skilled reader is expressly instructed to take measures to avoid that too much of the ML is being converted to menthol. All working examples disclose contents of unreacted menthol of less than 8%. This illustrates that almost complete conversion of menthol to ML and obtaining pure ML are key features of the teaching of WO2007/044146.

BRIEF DESCRIPTION OF THE INVENTION

The above problem could, surprisingly, be solved by generating in situ mixtures of menthol and menthyl lactate (in a particular ratio range, as defined below) by the partial esterification of lactic acid with menthol followed by controlled hydrolysis of higher esters. The ready to use composition(s) of the invention is (are) obtained on work-up and finally by vacuum distillation. This ready to use compositions can have different ratios of menthol and menthyl lactate which can be directly used in various products.

It was also observed that the composition of the reaction mixture before distillation should be such that the weight range of M to ML is from 15:85 to 60:40, or from 20:80 to 40:60, like preferably in the range of 30:70 (M:ML).

It was observed that, if the percentage of menthol in the reaction mixture is substantially lower or higher than this, the desired composition is not obtained. By carrying out fractional distillation, the desired composition may be collected successfully. In a particular embodiment of the invention, for example, the following three preferred compositions, namely, M:ML=75:25, 50:50 and 25:75 (wt/wt), are provided.

Preparing said three different types of M:ML mixtures allows to take the advantage of the excellent initial cooling sensation of menthol and the long lasting cooling effect of menthyl lactate or to take advantage of a balanced effect of both constituents. Thus, three compositions are provided, in such a way that a first composition will have the equal proportion of menthol and menthyl lactate (1:1), while the second and the third composition will be in the ratio of 3:1 and 1:3, respectively. This allows to make use of said composition having more menthol, in products where strong initial cooling is required, as for example toothpaste, shaving cream, chewing gum, candy mouthwash etc., while said composition with more of menthyl lactate can be used in scents, body lotion, hand wash, body creams etc. where a long lasting cooling effect is desired.

When determining the crystallization points of the compositions of the invention, it was noticed that the crystallization points of such compositions were found to be lower than those of the "Artificial Composition" by about 7 to 8° C. The obtained product is a ready to use liquid composition having a much lower crystallization point, thus making it convenient for cold processes and benefiting customers as it will simplify their large scale industrial processes in terms of cost, energy consumption and safety. Thus, the product is bound to attract the customers not only because it makes the formulation much simpler but also because the composition gives excellent initial cooling that comes from menthol, and long lasting cooling sensation due to menthyl lactate. Thus, the product also is characterized by a significant technical effect.

The required compositions are made from fairly low cost raw materials like menthol and lactic acid. These compositions are generally used in very small quantities, 1-2% by weight. The yield is quantitative. The process of manufacture is simple to operate. All these factors make the process highly economical.

US 2004/10018954 discloses compositions containing menthol and menthyl lactate in a ratio by weight in the range of 1:4-4:1 and where the crystallization point is below room temperature. Said prior art document reported the crystallization points for three compositions, namely M:ML; 75:25, 50:50, 25:75, as 21.5° C., 8.2° C. and 20.5° C., respectively.

The crystallization point of the compositions of the present invention is 7-8° C. lower than the crystallization point of the same compositions made by physical mixing.

BRIEF DESCRIPTION OF DRAWINGS

FIG. 1 illustrates a preferred reaction scheme of a process of the present invention.

PREFERRED EMBODIMENTS OF THE INVENTION

1. General Definitions

Unless otherwise stated the following general definitions shall apply:

"Lactic acid" encompasses D-(−)-lactic acid and (L-(+)-lactic acid (or simply D- and L-lactate).

"Menthol" encompasses each stereoisomer, i.e. (+)-menthol, (+)-isomenthol, (+)-neomenthol, (+)-isoneomenthol, (−)-menthol, (−)-isomenthol, (−)-neomenthol, and (−)-isoneomenthol alone or in any combination.

(−)-Menthol is also called L-menthol or (1R,2S,5R)-menthol, and has the following chemical structure:

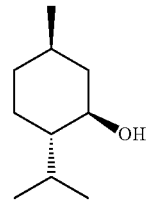

Menthyl monolactate is also called menthyl lactate and designates in particular the stereoisomer L-menthyl L-lactate (abbreviated as ML) of the formula:

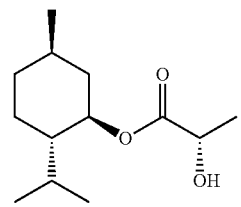 [SMILES: CC(C)[C@@H]1CC[C@@H](C)C[C@H]1OC(=O)[C@H](C)O]

Higher lactic acid menthyl esters are menthyl lactoyl lactate and menthyl lactoyl lactoyl lactate, and in particular the stereoisomers: L-menthyl L-lactoyl L-lactate (abbreviated as MLL) and L-menthyl L-lactoyl L-lactoyl L-lactate (abbreviated as MLLL).

"Ambient conditions" refer to T=21° C. and 1 atm (or 760 mm Hg) pressure.

"Essentially consisting of" menthol and a menthyl monolactate, refers to compositions containing impurities in the range of less than 0.5 wt %, like 0 to 0.4, 0.01 to 0.25 or 0.05 to 0.1 wt.-%, based on the total weight of the composition of the invention.

"Artificial compositions" of menthol and methyl lactate designate those compositions as obtained by physically admixing said constituents.

"Vacuum distillation" means performing a distillation under reduced pressure, in particular in a tange of 0.1 to 10 mbar, like 2 to 8 or, more particularly, 4 to 7 mbar.

2. Particular Embodiments

The present invention relates to the following particular embodiments

1. A method for preparing a composition essentially consisting of menthol and a menthyl lactate (i.e. a menthyl-monolactate) and which composition is liquid at ambient conditions, in particular at T=21° C. and 1 atm pressure (760 mm of Hg), and which method comprising the steps of:
a) partially esterifying menthol with lactic acid in a non-aqueous solvent to obtain a mixture of menthol and lactic acid methyl ester (ML) and higher lactic acid menthyl esters;
b) reacting the mixture obtained in step a) in order to selectively hydrolyze said higher lactic acid menthyl esters; and
c) isolating from the reaction mixture of step b) said liquid composition essentially consisting of menthol and a menthyl lactate.

In particular, the present invention is applicable to any stereoisomer form of menthol and lactic acid (as free acid or in the form of its salts, in particular as free acid). However, the present invention preferably makes use of (−) menthol and L-(+) lactic acid.

2. The method of embodiment 1, wherein in step a) menthol and lactic acid (in particular (−) menthol and L-(+) lactic acid) initially are present in a molar ratio in the range of about 1:1 to 1:2, and in particular about 1:1.5.

3. The method of embodiment 1 or 2, wherein the reaction in step a) is performed in the presence of an acidic catalyst, like in particular sulfuric acid.

4. The method of one of the preceding embodiments, wherein a partial esterification of menthol is performed in step a) such that menthol in a proportion of about 15 to 60% wt/wt, like about 20 to 40% wt/wt, as determined by gas chromatography under conditions as defined below (see experimental part), based on the originally added amount of menthol is not esterified. In particular, lactic acid is completely consumed.

5. The method according to any one of the preceding embodiments, wherein the non-aqueous solvent of step a) is water immiscible, and preferably selected from aliphatic and aromatic water-immiscible solvents, in particular boiling in the range of about 80 to 125° C. (at atmospheric pressure), as for example aliphatic solvents, like for example higher alkanes, in particular hexane, heptane or octane; or aromatic solvents, like for example benzene and toluene.

6. The method of anyone of the preceding embodiments wherein the esterification of step a) is performed while removing water produced during esterification, as for example by distillation.

7. The method of one of the preceding embodiments, wherein the ester hydrolysis of higher lactic acid menthyl esters of step b) is performed under temperature control, in particular in a temperature range of 20 to 40° C., like about 30° C., and at atmospheric pressure.

8. The method of one of the preceding embodiments wherein the ester hydrolysis of higher lactic acid menthyl esters of step b) is performed at a pH of about 11 to 13.5, in particular 12 to 13, like 12.4 to 12.7. In particular it is performed by a gradual (step wise) alkalization of the reaction mixture by adding a base until a pH of about 11 to 13.5 in particular 12 to 13, like 12.4 to 12.7 is reached. In particular, an inorganic base like an alkali metal hydroxide, in particular NaOH, is applied 9. The method of one of the preceding embodiments wherein the isolation according to step c) of a liquid composition essentially consisting of menthol and a menthyl lactate is performed by distillation. Preferably, the weight ratio of menthol to menthyl lactate in the composition to be subjected to distillation should be in the range of 15:85 to 60:40, in particular 20:80 to 40:60 and preferably about 30:70 wt/wt.

10. The method of to any one of the preceding embodiments, wherein in step c) vacuum distillation, in particular of a 30:70 wt/wt mixture of menthol and menthyl lactate (in particular (−) menthol and (−) menthyl L-(+) lactate) is performed as follows:
at a pressure of approximately 5 mbar and
i) a temperature of up to 90° C. for obtaining a composition showing a weight ratio of menthol:menthyl lactate of approximately 75:25 (wt/wt), and/or
ii) a temperature range from 90° C. to 95° C. for obtaining a composition showing a weight ratio of menthol:menthyl lactate of approximately 50:50 (wt/wt), and/or
iii) a temperature range from 95° C. to 100° C. for obtaining a composition showing a weight ratio of menthol:menthyl lactate of approximately 25:75 (wt/wt).
One, two or each of said three fractions i), ii) and iii) are obtained by distillation.

11. A liquid composition essentially consisting of menthol and a menthyl monolactate (in particular (−) menthol and (−) menthyl L-(+) lactate) obtainable by a method according to any one of embodiments 1 to 10.

12. The liquid composition of embodiment 11, characterized by a crystallization point which is (at ambient conditions) approximately 7 to 8° C. below the corresponding crystallization point of a mixture of menthol and menthyl lactate at identical molar ratios but obtained by physically admixing pure menthol and pure menthyl lactate (in particular pure (−) menthol and pure (−) menthyl L-(+) lactate). "Pure" in this context preferably has the meaning of "analytically pure", i.e. contaminations are analytically not detectable, as for example menthol an and menthyl lactate are applied in p.a. (analytical) grade.

13. The liquid composition of embodiments 11 or 12, selected from a composition (preferably of (−) menthol and (−) menthyl L-(+) lactate) having
i) a crystallization point of about +13° C. to +15° C. and having a molar ratio of menthol:menthyl lactate of approximately 75:25; or
ii) a crystallization point of about +2° C. to −1° C. and having a molar ratio of menthol:menthyl lactate of approximately 50:50; or
iii) a crystallization point of about +12° C. to +14° C. and having a molar ratio of menthol:menthyl lactate of approximately 25:75.

14. The use of a liquid composition according to any one of embodiments 11 to 13 or prepared according to anyone of the embodiments 1 to 10 in food, cosmetic or oral care products.

15. The use of a liquid composition according to any one of embodiments 11 to 13 or prepared according to anyone of the embodiments 1 to 10 as ingredient of a product, selected from food products, confections, chewing gums, beverages, cosmetics, toothpastes, mouthwashes, shampoos, toiletries, lotions, skin care products, medications, pharmaceuticals, or as additive for any one of the preceding products.

16. A product as defined in embodiments 14 or 15 comprising a cooling amount of a composition according to any one of embodiments 11 to 13 or prepared according to anyone of the embodiments 1 to 10.

17. The use of a liquid composition according to any one of embodiments 11 to 13 or prepared according to anyone of the embodiments 1 to 10 as a cooling agent, flavouring agent and/or fragrance agent.
18. A method of providing a physiological cooling effect, which method comprises contacting a surface area of a mammalian body with a liquid composition according to any one of embodiments 11 to 13 or prepared according to anyone of the embodiments 1 to 10 or a product as defined in embodiment 16.
19. The use, method or product according to anyone of the embodiments 14 to 18 in combination with at least one further coolant, in particular selected from isopulegol, menthyl lactate, N-ethyl-3-p-menthane carboxamide, 2-isopropyl-N,2,3-trimethyl butanamide, N-ethoxycarbonylmethyl-3-p-menthane carboxamide, monomenthyl glutarate, monomenthyl succinate, WS-3, WS-23, Cooling agent-10, menthol ethylene glycol carbonate, menthol propylene glycol carbonate, and Menthone Glycerine Acetal (Frescolate MGA).
20. The method, composition, product or use according to anyone of the preceding embodiments wherein menthol is (−)-menthol and/or lactic acid is L-(+)-lactic acid.

Further particular embodiments of the method of the invention, which may be further specified by the particular embodiments as described herein, in particular by the above identified embodiments 2 to 20, are:

21. A method for preparing a composition essentially consisting of menthol and a menthyl lactate and which composition is liquid at ambient conditions, and which method comprising the steps of:
   a) partially esterifying menthol with lactic acid in a non-aqueous solvent to obtain a mixture of menthol and lactic acid menthyl ester (ML) and higher lactic acid menthyl esters; whereby menthol in a proportion of 15 to 60% wt/wt, based on the originally added amount of menthol is not esterified;
   b) reacting the mixture obtained in step a) in order to selectively hydrolyze said higher lactic acid menthyl esters; and
   c) isolating from the reaction mixture of step b) at least one liquid composition essentially consisting of menthol and a menthyl lactate by vacuum destillation, wherein the weight ratio of menthol to menthyl lactate in the composition to be subjected to distillation in step c) is in the range of 15:85 to 60:40 wt/wt.
22. A method for preparing a composition essentially consisting of menthol and a menthyl lactate and which composition is liquid at ambient conditions, and which method comprising the steps of:
   a) partially esterifying menthol with lactic acid in a non-aqueous solvent to obtain a mixture of menthol and lactic acid menthyl ester (ML) and higher lactic acid menthyl esters; whereby menthol in a proportion of 15 to 60% wt/wt, based on the originally added amount of menthol is not esterified;
   b) reacting the mixture obtained in step a) in order to selectively hydrolyze said higher lactic acid menthyl esters; and
   c) isolating from the reaction mixture of step b) at least one liquid composition essentially consisting of menthol and a menthyl lactate by vacuum distillation, wherein the weight ratio of menthol to menthyl lactate in the composition to be subjected to distillation in step c) is in the range of 15:85 to 60:40 wt/wt;
   and wherein at least one composition essentially consisting of menthol and a menthyl lactate is obtained, characterized by a crystallization point which is (at ambient conditions) approximately 7 to 8° C. below the corresponding crystallization point of a mixture of menthol and menthyl lactate at identical molar ratios but obtained by physically admixing pure menthol and pure menthyl lactate.
23. A method for preparing a composition essentially consisting of menthol and a menthyl lactate and which composition is liquid at ambient conditions, and which method comprising the steps of:
   a) partially esterifying menthol with lactic acid in a non-aqueous solvent to obtain a mixture of menthol and lactic acid menthyl ester (ML) and higher lactic acid menthyl esters; whereby menthol in a proportion of 15 to 60% wt/wt, based on the originally added amount of menthol is not esterified;
   b) reacting the mixture obtained in step a) in order to selectively hydrolyze said higher lactic acid menthyl esters; and
   c) isolating from the reaction mixture of step b) at least one liquid composition essentially consisting of menthol and a menthyl lactate by vacuum distillation, wherein the weight ratio of menthol to menthyl lactate in the composition to be subjected to distillation in step c) is in the range of 15:85 to 60:40 wt/wt;
   and wherein at least one composition essentially consisting of menthol and a menthyl lactate is obtained, selected from a composition having
   i) a crystallization point of about +13° C. to +15° C. and having a molar ratio of menthol:menthyl lactate of approximately 75:25;
   ii) a crystallization point of about +2° C. to −1° C. and having a molar ratio of menthol:menthyl lactate of approximately 50:50; and/or
   iii) a crystallization point of about +12° C. to +14° C. and having a molar ratio of menthol:menthyl lactate of approximately 25:75 is obtained.

3. Preferred Method of Preparing Particular Compositions of the Invention 3.1 Esterification:

A mixture of L-menthol and L-(+)-lactic acid in a molar ratio of about 1:1.5 and an appropriate catalytic amount of sulfuric acid in an water-immiscible solvent, like in heptane, was refluxed and water removed azeotropically. As the esterification proceeds in a temperature range of about 80 to 125° C. the solvent should be selected such that evaporation of the solvent is avoided. The reaction may be stopped at an appropriate point of time, for example when an amount of about 30% menthol remained unreacted. Preferably the entire amount of lactic acid is consumed at the end of the reaction. The reaction mixture then will be cooled to room temperature.

3.2 Controlled Hydrolysis:

The above mixture may be subjected to hydrolysis with an appropriate amount of base, as for example 50% sodium hydroxide, whereby the higher esters should be hydrolyzed to menthyl lactate.

If appropriate, additional organic solvent and or water may be added prior to hydrolysis. For example the partially esterified mixture is further diluted with water and heptane. The base, like sodium hydroxide (Aq. 50% NaOH) is then added lot wise under external cooling (cold water bath) so that the temperature does not exceed 25 to 35, in particular about 30° C. After each addition the mixture is stirred for sufficient time, as for example for 30 min. Then the pH is checked and the sample is analyzed by GC. Base addition is continued till the pH of the mixture reaches around pH 11.5 to 13, in particular 12.0 to 12.7. This guarantees the selective hydrolysis of higher lactoly esters while monoesters are not decomposed.

GC analysis at this point shows practically complete conversion of higher lactates MLL, MLLL into menthyl lactate with no hydrolysis of ML to menthol.

Initially it was assumed that selective hydrolysis would be difficult to achieve because the conditions that favour hydrolysis of higher esters to ML theoretically should favour hydrolysis of ML to menthol. But contrary to this it was, surprisingly, observed that hydrolysis of higher esters (MLL, MLLL etc) to ML (arresting further hydrolysis to menthol) can be achieved by controlling the two factors namely quantity of NaOH and temperature.

3.3 Separation:

The required composition is then obtained upon work-up and subsequent vacuum distillation in a manner known per se.

4. Preferred Use of the Liquid M/ML Compositions

The liquid compositions comprising menthol and menthyl lactate as prepared in the above manner are preferably used in an amount effective to provide a physiological cooling effect when formulated into a consumer product or contacted with mammalian skin or mucous membranes.

Preferably, the consumer product is a food, confection, chewing gum, beverage, cosmetic, toothpaste, mouthwash, shampoo, lotions, toiletry, shaving lotions, foams, creams gels, after-shaves, medication, pharmaceutical, or the like. Other and more particular suitable consumer product applications for physiological coolants have been described (see, e.g., U.S. Pat. Nos. 4,136,163 and 7,189,760).

The actual amount needed will depend on many factors, including the particular end-use application, desired cooling profile, identity and amounts of any other coolants in the composition, and other considerations. Normally, the amount needed is determined empirically by the skilled person. Generally, the amount used will be within the range of 0.1 ppm to 5 wt. % (50,000 ppm), preferably from 5 ppm to 1 wt. %. In a topical application such as a lotion or hand cream, for example, the amount of the composition required will typically range from 100 ppm to 5 wt. %. Low concentrations (0.1 ppm to 100 ppm) should be more suitable for beverages, while intermediate levels (10 ppm to 5,000 ppm) are normally desirable for a toothpaste, chewing gum, candy, or mouthwash.

The liquid composition of the invention may also be a liquid mixture that may contain one or more other physiological coolants. Preferably, such additional coolant may be selected from substituted cyclohexanols and their esters, carboxamides, menthone ketals, menthoxypropanediols, and mixtures thereof. Particular examples of additional coolants include menthol, isopulegol, menthyl lactate, N-ethyl-3-p-menthane carboxamide (WS-3), 2-isopropyl-N,2,3-trimethyl butanamide (WS-23), N-ethoxy-carbonylmethyl-3-p-menthane carboxamide (WS-5), monomenthyl glutarate, monomenthyl succinate, and mixtures thereof.

The invention will now be explained in more detail by making reference to the following examples:

Experimental Part:

A) General Methods

1. Determination of Crystallization Point:

A liquid sample was taken in a conical flask fitted with a thermometer. The liquid in the flask was stirred under slow cooling using acetone and dry ice. As the temperature of the mixture decreased, the liquid started thickening and, at one point, became turbid followed by slight increase in temperature. This point was recorded as the crystallization point.

2. GC Analysis:
   Instrument: Shimatzu-GC-2010, GC solutions
   Column: HP-5, 30 mm*0.25 mm*0.25 µm
   Flow 1.32 ml/min, INJ: 0.5 µL
   INJ: 250° C. DET: 300° C.
   Temp. Program: 50° C.-0-10° C./min-280° C.-20 min 3. NMR Analysis:
   Instrument: Bruker 300 MHz, BBO probe
   NMR in $CDCl_3$ Example 1

Preparation of Composition of Menthol and Menthyl Lactate by Esterification (without Acid Catalysis) and Controlled Hydrolysis Followed by Fractional Distillation Esterification:

A three-neck flask equipped with a dean Stark trap, thermometer, oil bath and magnetic stirrer is charged with L-menthol (20 g, 0.128 mol), L-(+)-lactic acid (26.2 g, 0.256 mol, 88%, pure) and heptane (10 g). The stirred mixture is refluxed and water is removed azeotropically. The heating (bath temp 130° C.) was stopped when temperature of the mixture increases gradually to 125° C. after 13.5 h and after 6.4 ml water was removed and about 30% menthol remained unreacted. The mixture was cooled to room temperature and analyzed by gas chromatography (GC). It contains: 29.33% unreacted menthol, 38.52% of l-menthyl lactate (ML), 18.02% l-menthyl lactoyl lactate (MLL) and 5.25% l-menthyl lactoyl lactoyl lactate (MLLL) and some lactide.

Controlled Hydrolysis:

The partially esterified mixture is diluted with water (16 g) and heptane (10 ml). Aq. sodium hydroxide (16 g of 50% NaOH) was then added drop wise over 30 min. under external cooling (cold water bath) so that the temperature does not exceed 30° C. and the pH does not exceed 14. After the base addition, mixture was stirred for another 2.5 h. GC analysis shows practically complete conversion of higher lactates into menthyl lactate and the GC contains: 49.32% of unreacted menthol and 49.66% of ML (the use of excess NaOH hydrolysed some methyl lactate into menthol). The layers were separated. The organic layer washed with 5% aq. Lactic acid (10 g) and then dried over sodium sulfate. The solvent removed on Rotavapor to get residue (23.5 g).

Fractional Distillation:

Residue (23.5 g) was fractionally distilled using Perkin Triangle under constant vacuum at 6.5 mbar and obtained following fractions.

| Fractions | Temp range | Pressure | weight, (g) | M % | ML % |
|---|---|---|---|---|---|
| Fr - 1 | up to 90° C. | 6.5 mbar | 2.00 | 80.17 | 18.17 |
| Fr - 2 | 90-95° C. | 6.5 mbar | 6.64 | 70.84 | 28.24 |
| Fr - 3 | 95-105° C. | 6.5 mbar | 3.63 | 21.01 | 77.76 |
| Fr - 4 | 105-115° C. | 6.5 mbar | 5.95 | 1.6 | 82.75 |
| Fr - 5 | 115-117° C. | 6.5 mbar | 3.96 | 1.38 | 94.75 |
| Total | | | 22.18 | | |

Example 2

Preparation of Composition of Menthol and Menthyl Lactate by Acid Catalyzed Esterification and Controlled Hydrolysis Followed by Fractional Distillation Esterification:

The procedure of Example 1 is generally followed using L-menthol (20 g, 0.128 mol), L-(+)-lactic acid (20 g, 0.195 mol, 88%, pure), heptane (10 g) and conc. $H_2SO_4$ (0.12 g). The temperature of the mixture increases gradually to 120° C. after 7 h and after 4.8 ml water was removed and about 20% menthol remained unreacted. The mixture was cooled to room temperature and analyzed by gas chromatography (GC). It contains: 20.79% unreacted menthol, 43.39% of ML, 22.95% of MLL, 7.40% of MLLL and some lactide.

Controlled Hydrolysis:

The partially esterified mixture is diluted with water (16 g) and heptane (15 ml). Aq. Sodium hydroxide (9.3 g of 50% NaOH) was then added drop wise over 30 min. under external cooling (cold water bath) so that the temperature does not exceed 30° C. and the pH does not exceed 12.5. After the base addition, mixture was stirred for another 2.5 h. pH was 12. GC analysis shows practically complete conversion MLL and MLLL into ML. GC shows: 22.60% of unreacted menthol, 75.44% of ML and 0.52% of MLL. The layers were separated. The organic layer washed with water (20 g) and then dried over sodium sulfate. The solvent removed on Rota vapor to get the residue (23 g)

Fractional Distillation:

Residue (23 g) was fractionally distilled using Perkin Triangle under constant vacuum at 5 mbar and obtained the following fractions

| Fractions | Temp range | Pressure | weight, (g) | M % | ML % |
|---|---|---|---|---|---|
| Fr - 1 | Up to 90° C. | 5 mbar | 10 | 49.38% | 48.64% |
| Fr - 2 | 90-110° C. | 5 mbar | 4.5 | 1.32% | 98.55% |
| Fr - 3 | 110-112° C. | 5 mbar | 7 | 0.20% | 99.20% |
| Total | | | 21.5 | | |

Example 3

Preparation of Composition of Menthol and Menthyl Lactate by Acid Catalyzed Esterification and Controlled Hydrolysis Followed by Fractional Distillation Esterification:

The procedure of example 1 is generally followed using L-menthol (100 g, 0.64 mol), L-(+)-lactic acid (100 g, 0.97 mol, 88%, pure), heptane (50 g) and conc. $H_2SO_4$ (0.6 g). The temperature of the mixture increases gradually to 120° C. after 4 h and after 29 ml water was removed and about 15% menthol remained unreacted. The mixture was cooled to room temperature and analyzed by gas chromatography (GC). It contains: 14.15% unreacted menthol, 50.61% of ML, 22.88% of MLL, 7.97% of MLLL and some lactide.

Controlled Hydrolysis:

The partially esterified mixture is diluted with water (80 g) and heptane (50 ml). Aq. sodium hydroxide (35 g of 50% NaOH) was then added drop wise over 30 min. under external cooling (cold water bath) so that the temperature does not exceed 30° C. and the pH does not exceed 12.5. After the base addition, mixture was stirred for another 2.5 h. pH was 11. GC analysis shows practically complete conversion of MLL and MLLL into ML. GC shows: 15.18% of unreacted menthol, 83.51% of ML and 0.66% of MLL. The layers were separated. The organic layer washed with 2% lactic acid (20 g), dried over sodium sulfate. The solvent removed on Rota vapor to get the residue (125 g).

Fractional Distillation:

Residue (125 g) was fractionally distilled using Perkin Triangle under constant vacuum at 5 mbar and obtained the following fractions.

| Fractions | Temp range | Pressure | weight, (g) | M % | ML % |
|---|---|---|---|---|---|
| Fr - 1 | Up to 64° C. | 5 mbar | 3.3 | 73.32 | 24.35 |
| Fr - 2 | 64-86° C. | 5 mbar | 3.78 | 72.86 | 25.19 |
| Fr - 3 | 86-96° C. | 5 mbar | 12.89 | 56.45 | 42.5 |
| Fr - 4 | 96-110° C. | 5 mbar | 13.12 | 24.84 | 74.72 |
| Fr - 5 | 110-112° C. | 5 mbar | 87 | 0.76 | 99.23 |
| Total | | | 120 | | |

Example 4

Preparation of Composition of Menthol and Menthyl Lactate by Acid Catalyzed Esterification and Controlled Hydrolysis Followed by Fractional Distillation Esterification:

The procedure of example 1 is generally followed except, bath temp. 140° C., using L-menthol (100 g, 0.64 mol), L-(+)-lactic acid (100 g, 0.97 mol, 88%, pure), heptane (50 g) and conc. $H_2SO_4$ (0.6 g). The temperature of the mixture increases gradually to 125° C. after 2 h and after 24 ml water was removed and about 30% of menthol remained unreacted. The mixture was cooled to room temperature and analyzed by (GC). It contains: 29.07% unreacted menthol, 46.69% of ML, 14.13% of MLL, 3.32% of MLLL and some lactide.

Controlled Hydrolysis:

The partially esterified mixture is diluted with water (80 g) and heptane (50 ml). Aq. sodium hydroxide (46 g of 50% NaOH) was then added drop wise over 30 min. under external cooling (cold water bath) so that the temperature does not exceed 30° C. and the pH does not exceed 13. After the base addition, mixture was stirred for another 2.5 h. pH was 12.6 GC analysis shows practically complete conversion MLL and MLLL into ML. GC shows: 28.38% of unreacted menthol, 69.16% of ML and 0.37% of MLL. The layers were separated. The organic layer washed with 1% lactic acid (50 ml), dried over sodium sulfate. The solvent removed on Rota vapor to get 128 g residue.

Fractional Distillation:

This residue was divided into three parts to carry out three different fractional distillations keeping the vacuum constant at 5 mbar and collecting the fractions at different temp. range. The results are tabulated as below

Example 4A

Residue Used=42 g

| Fractions | Temp range | Pressure | weight, (g) | M % | ML % |
|---|---|---|---|---|---|
| Fr - 1 | up to 90° C. | 5 mbar | 8.77 | 75.3 | 23.37 |
| Fr - 2 | 90-95° C. | 5 mbar | 5.00 | 53.83 | 44.93 |
| Fr - 3 | 95-100° C. | 5 mbar | 5.60 | 22.21 | 77.67 |
| Fr - 4 | 100-104° C. | 5 mbar | 16.00 | 1.93 | 97.73 |
| Fr - 5 | 104-107° C. | 5 mbar | 3.75 | 0.43 | 98.61 |
| Total | | | 39.12 | | |

Example 4B

Residue Used=42 g

| Fractions | Temp range | Pressure | weight, (g) | M % | ML % |
|---|---|---|---|---|---|
| Fr - 1 | up to 90° C. | 5 mbar | 12.15 | 72.93 | 26.29 |
| Fr - 2 | 90-100° C. | 5 mbar | 5.80 | 39.97 | 59.78 |
| Fr - 3 | 100-107° C. | 5 mbar | 21.00 | 3.22 | 96.77 |
| Total | | | 38.95 | | |

Example 4C

Residue Used=42 g

| Fractions | Temp range | Pressure | weight, (g) | M % | ML % |
|---|---|---|---|---|---|
| Fr - 1 | up to 90° C. | 5 mbar | 10.00 | 75.68 | 23.01 |
| Fr - 2 | 90-97° C. | 5 mbar | 6.85 | 45.66 | 53.92 |
| Fr - 3 | 97-103° C. | 5 mbar | 9.84 | 13.76 | 86.16 |
| Fr - 4 | 103-107° C. | 5 mbar | 9.20 | 1.16 | 98.83 |
| Total | | | 35.89 | | |

Example 5

Comparative Example

Fractionation of Artificially Prepared Composition of Menthol and Menthyl Lactate (40:60)

Artificial Composition of M and ML was prepared as described below. Weighed 16 g menthol and 2 g menthyl lactate in a round bottom flask, heated to 5° C. under slow stirring till clear liquid was obtained.

Wt. of the liquid was 4 g, and GC shows: 40.6% of menthol and 59.22% of ML. It was fractionally distilled under vacuum (5 mbar) and following fractions were collected

| Fractions | Temp range | Pressure | weight, (g) | M % | ML % |
|---|---|---|---|---|---|
| Fr - 1 | up to 90° C. | 5 mbar | 14.80 | 81.98 | 17.37 |
| Fr - 2 | 90-95° C. | 5 mbar | 3.35 | 51.04 | 48.95 |
| Fr - 3 | 95-103° C. | 5 mbar | 20.50 | 8.57 | 91.29 |
| Total | | | 38.65 | | |

Example 6

Preparation of Composition of Menthol and Menthyl Lactate by Acid Catalyzed Esterification and Controlled Hydrolysis Followed by Fractional Distillation Esterification:

The procedure of example 1 is generally followed using L-menthol (100 g, 0.64 mol), L-(+)-lactic acid (100 g, 0.97 mol, 88%, pure), heptane (50 g) and conc. $H_2SO_4$ (0.6 g). The temperature of the mixture increases gradually to 120° C. after 3 h and after 24 ml water was removed and about 20% of menthol remained unreacted. The mixture was cooled to room temperature and analyzed by gas chromatography (GC). It contains: 21.36% unreacted menthol, 54.24% of ML, 17.68% of MLL, 4.08% of MLLL and some lactide.

Controlled Hydrolysis:

The partially esterified mixture is diluted with water (80 g) and heptane (50 ml). Aq. Sodium hydroxide (46 g of 50% NaOH) was then added drop wise over 30 min. under external cooling (cold water bath) so that the temperature does not exceed 30° C. and the pH does not exceed 12.5. After the base addition, mixture was stirred for another 1 h. pH at this stage was 11.5

GC analysis shows practically complete conversion MLL and MLLL into ML. GC shows: 23.22% of unreacted menthol, 75.97% of ML and 0.16% of MLL. The reaction mixture was left standing overnight. GC analysis shows: 25.30% menthol and 73.77% ML, which indicates that Menthyl lactate slowly hydrolyses to menthol on prolonged standing at higher pH. The layers were separated. The organic layer washed with 1% lactic acid (50 ml), dried over sodium sulfate. The solvent removed on Rota vapor to get 130 g residue Fractional Distillation This residue was divided into two equal parts to carry out two different fractional distillations keeping the vacuum constant at 5 mbar and collecting the fractions at different temperature range. The results are as below.

Example 6 A

Residue Used=65 g

| Fractions | Temp range | Pressure | weight, (g) | M % | ML % |
|---|---|---|---|---|---|
| Fr - 1 | up to 72° C. | 5 mbar | 0.50 | Not done | Not done |
| Fr - 2 | 72-90° C. | 5 mbar | 16.50 | 71.27 | 28.52 |
| Fr - 3 | 90-105° C. | 5 mbar | 40.50 | 13.43 | 86.56 |
| Fr - 4 | 105-107° C. | 5 mbar | 1.50 | Not done | |
| Total | | | 59.00 | | |

Example 6 B

Residue Used=65 g

| Fractions | Temp range | Pressure | weight, (g) | M % | ML % |
|---|---|---|---|---|---|
| Fr - 1 | up to 72° C. | 5 mbar | 0.50 | Not done | Not done |
| Fr - 2 | 72-105° C. | 5 mbar | 57.00 | 25.7 | 73.63 |
| Total | | | 57.5 | | |

Example 6B shows that if the crude composition (25.30% of M and 73.77% of ML) is distilled as one fraction, we get that composition in very pure form. Here the advantage is that no fractionation is needed.

Example 7

Preparation of Composition of Menthol and Menthyl Lactate by Esterification and Controlled Hydrolysis Followed by Fractional Distillation Esterification:

The procedure of example 1 is generally followed using L-menthol (40 g, 0.256 mol), L-(+)-lactic acid (52.4 g, 0.512 mol) 88%, pure), heptane (20 g). The temperature of the mixture increases gradually to 120° C. after 1 h and after 5 ml water was removed and about 60% menthol remained unreacted. The mixture was cooled to room temperature and analyzed by gas chromatography (GC). It contains: 62.97% of unreacted menthol, 22.34% of ML, 5.94% of MLL, 0.5% of MLLL and some lactide.

Controlled Hydrolysis:

The partially esterified mixture is diluted with water (16 g) and heptane (15 ml). Aq. sodium hydroxide (10 g of 50% NaOH) was then added drop wise over 30 min. under external cooling (cold water bath) so that the temperature does not exceed 30° C. and the pH does not exceed 12.5. After the base addition, mixture was stirred for another 1 h. pH at this stage was 11.5

GC shows: 64.90% of unreacted menthol and 34.82% of ML Worked up as usual to get residue (41 g).

Fractional Distillation:

Residue (37.5 g) was fractionally distilled under vacuum (5 mbar) to obtain the following fractions.

| Fractions | Temp range | Pressure | weight, (g) | M % | ML % |
|---|---|---|---|---|---|
| Fr - 1 | up to 82° C. | 5 mbar | 17.62 | 90.84 | 8.80 |
| Fr - 2 | 82-90° C. | 5 mbar | 5.24 | 80.07 | 19.81 |
| Fr - 3 | 90-100° C. | 5 mbar | 12.72 | 24.91 | 74.67 |

Fraction 1 and 2 having a menthol content of more than 80% solidifies on standing. This example shows that if the percentage of menthol in the crude composition is more (>30%), fractions will contain more of menthol and we may not get the desired compositions (75:25 and 50:50) and fractions containing menthol more that around 80% solidify.

Example 8

Preparation of Composition of Menthol and Menthyl Lactate by Acid Catalyzed Esterification and Controlled Hydrolysis Followed by Fractional Distillation Esterification:

The general procedure of esterification (example 1, described earlier) is generally followed using L-menthol (750 g, 4.81 mol), L-(+)-lactic acid (750 g, 7.33 mol, 88%, pure), heptane (400 g) and conc. $H_2SO_4$ (4.5 g). The temperature of the mixture increases gradually to 125° C. after 4 h and after 175 ml water was removed and about 15% of menthol remained unreacted. The mixture was cooled to room temperature and analyzed by (GC). It contains: 14.99% of unreacted menthol, 56.86% of ML, 19.31% of MLL, 4.84% of MLLL and some lactide.

Reaction mixture was divided into two equal parts to carry out controlled hydrolysis separately at two different conditions.

Example 8A

Controlled Hydrolysis of Part-1:

The partially esterified mixture (part-1) is diluted with water (300 g) and heptane (200 ml). Aq. sodium hydroxide (300 g of 50% NaOH) was then added drop wise over 1 h under external cooling (cold water bath) so that the temperature does not exceed 30° C. and the pH does not exceed 14.5. After the base addition, mixture was stirred for another 2 h. (pH was 14). GC analysis shows complete conversion of MLL and MLLL into ML.

GC shows: 28.38% of unreacted menthol, 69.16% of ML. The layers were separated. The organic layer washed with 5% lactic acid (100 ml), dried over sodium sulfate. The solvent removed on Rota vapor to get 470 g residue.

Fractional Distillation:

Residue (460 g) was fractionally distilled using Perkin Triangle under constant vacuum (5 mbar) and obtained following fractions

| Fractions | Temp range | Pressure | weight, (g) | M % | ML % |
|---|---|---|---|---|---|
| Fr - 1 | up to 90 | 5 mbar | 57 | 62.58 | 37.08 |
| Fr - 2 | 90-95 | 5 mbar | 85 | 45.71 | 54.13 |
| Fr - 3 | 95-100 | 5 mbar | 86 | 27.14 | 72.85 |
| Fr - 4 | 100-105 | 5 mbar | 36 | 18.85 | 79.00 |
| Fr - 5 | 105-108 | 5 mbar | 143 | 2.35 | 97.04 |
| Total | | | 407 | | |

Example 8B

Controlled Hydrolysis of Part-2:

The partially esterified mixture (part-2) is diluted with water (300 g) and heptane (200 ml). Reaction mixture heated to 50° C. and aq. sodium hydroxide (170 g of 50% NaOH) was then added drop wise over 1 h. After the base addition is complete, mixture was stirred at 50° C. for another 1 h. (pH was 11.5). GC analysis shows complete conversion of MLL and MLLL into ML.

GC shows: 30.66% of unreacted menthol, 68.18% of ML. The layers were separated. The organic layer washed with 1% lactic acid (100 ml), dried over sodium sulfate. The solvent removed on Rota vapor to get 480 g residue.

Fractional Distillation:

Residue (470 g) was fractionally distilled using Perkin Triangle under constant vacuum (5 mbar) and obtained following fractions

| Fractions | Temp range | Pressure | weight, (g) | M % | ML % |
|---|---|---|---|---|---|
| Fr - 1 | up to 90 | 5 mbar | 113 | 73.41 | 26.18 |
| Fr - 2 | 90-95 | 5 mbar | 63 | 53.53 | 46.31 |
| Fr - 3 | 95-100 | 5 mbar | 60 | 24.90 | 74.95 |
| Fr - 4 | 100-105 | 5 mbar | 42 | 5.14 | 94.00 |
| Fr - 5 | 105-115 | 5 mbar | 145 | 0.196 | 99.43 |
| Total | | | 423 | | |

Discussion of Experimental Results:

Example 1: It was observed that: 1) if more than the required quantity of NaOH is used for hydrolyzing higher esters then some of the menthyl lactate is also hydrolyzed to menthol. 2) If acid is not used as a catalyst then reaction time is too long.

Example 2: It was observed that 1) if the reaction is catalyzed by acid such as $H_2SO_4$, the reaction time is reduced considerably and 2) if the initial mixture contains unreacted menthol that is less than 30% wt/wt then we don't get the desired composition. Here when the menthol percentage was about 20%, the first composition (up to 90° C.) was about 50:50 instead of 75:25 wt/wt by GC.

Example 3: It was observed that even if the percentage of menthol in the initial mixture is less than 30%, one still can obtain one and/or two desired composition (out of three) if the temperature range is adjusted accordingly.

In this example the percentage of menthol in the initial mixture was about 15%. Fraction-1 (up to 86° C.) was about 75:25 (i.e. first desired composition) and the fraction-3 (96 to 110° C.) was about 25:75 (i.e. third desired composition) Thus, even if the initial ratio is not 30%, the experiment does not go waste.

Example 4: It was observed that when a mixture of menthol:menthyl lactate in the ratio 30:70 is vacuum distilled at 5 mbar pressure, the following fractions are obtained:
Fraction up to 90° C. containing M:ML in the ratio of 75:25, yield 25% (w/w).
Fraction between 90-95° C. containing M:ML in the ratio of 50:50, yield 14-15%
Fraction between 95-100° C. containing M:ML in the ratio of 25:75, yield 12-13%;
Fraction above 100° C. contains mainly menthyl lactate.
Thus, around 50% of the product is obtained in different compositions while the rest is menthyl lactate.

Example 5 (Comparative Example): Here it was observed that when we carry out distillation of an artificially prepared mixture having a percentage of menthol of more than 30% (like 60%), then we get the fractions containing more of menthol. This observation was in line with the same ratio obtained in the Example 7 (see results of Example 7)

Example 6: One example was done (Example 6B) where only one fraction was collected to get a 25:75 mixture of M:ML in 88% (w/w) yield. This fraction was divided into 3 parts, one was kept at 25:75, the second and third were adjusted to 50:50 and 75:25 by adding a calculated quantity of menthol. The advantage here is that, since this fraction is in liquid form, it is easy to mix with solid menthol.

Example 7: As in the case of example 6, here it was also observed that if the percentage of menthol in the initial reaction mixture is more than 30% (here it is 60%)) then first two fractions contained 90% and 80%, respectively, of menthol and solidified on standing.

Example 8A: Here it is observed that the use of excess NaOH has also hydrolyzed some of ML into menthol. Said data further confirm that an optimum pH range is in the range of 11.5 to 13 but more preferably 12.5.

Example 8B: Here also it is observed that some of the ML gets hydrolyzed into menthol, as the hydrolysis was done at higher temperature (50° C.). It illustrates that temperature also is critical during the hydrolysis step.

Based on the results of the above examples following conclusions may be drawn:
1) That a ratio of about 30:70 of M:ML is most ideal to get the three desired compositions.
2) That the pH of the reaction mixture during hydrolysis should not be more than about 12.5
3) Hydrolysis should be carried preferably at about 30° C.

Formulation Example:

Example 9

Freshening Shower Gel

A freshening shower gel prepared by applying a liquid M/ML composition of the invention is prepared in conventional manner. The shower gel comprises the following compounds in percentage by weight:

| Compounds | % by weight |
|---|---|
| Sodium laureth sulfate | 12 |
| Hydroxypropyl methylcellulose | 0.5 |
| Sodium cocoyl isethionate | 7 |
| Ammonium lauryl sulfate | 3 |
| Lauryl glucoside | 1 |
| Lauryl betaine | 4 |
| Polyquaternium-10 | 5 |
| Polyethylene glycol (PEG) | 2 |
| Preservative (s) | 0.5 |
| Fagrance | 1.5 |
| Menthyl lactate/menthol 25:75 | 1.5 |
| Water | ad 100 |

The documents referenced herein are all incorporated by reference.

The invention claimed is:

1. A method for preparing a composition consisting essentially of menthol and menthyl lactate (ML) and which composition is liquid at ambient conditions, the method comprising:
   a) partially esterifying menthol with lactic acid in a non-aqueous solvent to obtain a mixture of menthol, lactic acid menthyl ester, and higher lactic acid menthyl esters; whereby menthol in a proportion of 15 to 60% wt/wt, based on the originally added amount of menthol, is not esterified;
   b) reacting the mixture obtained in step a) in order to hydrolyze said higher lactic acid menthyl esters; and
   isolating from the reaction mixture of step b) at least one liquid composition consisting essentially of menthol and menthyl lactate, wherein the concentration of menthol in the at least one liquid composition is at least 30% wt/wt;
      wherein in step c) vacuum distillation is performed as follows: at a pressure of approximately 5 mbar and
      i) a temperature of up to 90° C. for obtaining a composition having a weight ratio of menthol:menthyl lactate (ML) of approximately 75:25 (wt/wt), or ii) a temperature range from 90° C. to 95° C. for obtaining a composition having a weight ratio of menthol:menthyl lactate (ML) of approximately 50:50(wt/wt), or iii) a temperature range from 95° C. to 100° C. for obtaining a composition having a weight ratio of menthol:menthyl lactate (ML) of approximately 25:75 (wt/wt).

2. The method of claim 1, wherein in step a) menthol and lactic acid initially are present in a molar ratio in the range of 1:1 to 1:2.

3. The method of claim 1, wherein the reaction in step a) is performed in the presence of an acidic catalyst.

4. The method of claim 1, wherein a partial esterification of menthol is performed in step a) such that menthol in a proportion of 20 to 40% wt/wt, based on the originally added amount of menthol, is not esterified.

5. The method according to claim 1, wherein the non-aqueous solvent of step a) is water immiscible.

6. The method of claim 1, wherein the esterification of step a) is performed while removing water produced during esterification.

7. The method of claim 1, wherein the ester hydrolysis of higher lactic acid menthyl esters of step b) is performed under temperature control and at atmospheric pressure.

8. The method of claim 1, wherein the ester hydrolysis of higher lactic acid menthyl esters of step b) is performed at a pH of about 11 to 13.5.

9. The method of claim 1, wherein a liquid composition is obtained, characterized by a crystallization point which is (at ambient conditions) approximately 7 to 8° C. below the corresponding crystallization point of a mixture of menthol and menthyl lactate at identical molar ratios but obtained by physically admixing pure menthol and pure menthyl lactate.

10. The method of claim 1, wherein the liquid composition is selected from the group consisting of:

i) a composition having a crystallization point of about +13° C. to +15° C. and having a molar ratio of menthol:menthyl lactate of approximately 75:25;

ii) a composition having a crystallization point of about +2° C. to −1° C. and having a molar ratio of menthol:menthyl lactate of approximately 50:50; and iii) a composition having a crystallization point of about +12° C. to +14° C. and having a molar ratio of menthol:menthyl lactate of approximately 25:75.

11. A method for preparing a composition consisting essentially of menthol and menthyl lactate (ML) and which composition is liquid at ambient conditions, the method comprising:

a) partially esterifying menthol with lactic acid in a non-aqueous solvent to obtain a mixture of menthol, lactic acid menthyl ester, and higher lactic acid menthyl esters; whereby menthol in a proportion of 15 to 60% wt/wt, based on the originally added amount of menthol is not esterified;

b) reacting the mixture obtained in step a) in order to hydrolyze said higher lactic acid menthyl esters; and c) isolating from the reaction mixture of step b) at least one liquid composition essentially consisting of menthol and a menthyl lactate by vacuum distillation, wherein the weight ratio of menthol to menthyl lactate in the composition to be subjected to distillation in step c) is in the range of 15:85 to 60:40 wt/wt.

12. A method for preparing a composition consisting essentially of menthol and menthyl lactate (ML) and which composition is liquid at ambient conditions, the method comprising:

a) partially esterifying menthol with lactic acid in a non-aqueous solvent to obtain a mixture of menthol, lactic acid menthyl ester, and higher lactic acid menthyl esters; whereby menthol in a proportion of 15 to 60% wt/wt, based on the originally added amount of menthol, is not esterified;

b) reacting the mixture obtained in step a) in order to hydrolyze said higher lactic acid menthyl esters; and c) isolating from the reaction mixture of step b) at least one liquid composition essentially consisting of menthol and menthyl lactate (ML) by vacuum distillation, wherein the weight ratio of menthol to menthyl lactate (ML) in the composition to be subjected to distillation in step c) is in the range of 15:85 to 60:40 wt/wt;

and wherein at least one composition essentially consisting of menthol and menthyl lactate is obtained, characterized by a crystallization point which is (at ambient conditions) approximately 7 to 8° C. below the corresponding crystallization point of a mixture of menthol and menthyl lactate at identical molar ratios but obtained by physically admixing pure menthol and pure menthyl lactate.

13. A method for preparing a composition consisting essentially of menthol and menthyl lactate (ML) and which composition is liquid at ambient conditions, the method comprising:

a) partially esterifying menthol with lactic acid in a non-aqueous solvent to obtain a mixture of menthol, lactic acid menthyl ester, and higher lactic acid menthyl esters; whereby menthol in a proportion of 15 to 60% wt/wt, based on the originally added amount of menthol, is not esterified;

b) reacting the mixture obtained in step a) in order to hydrolyze said higher lactic acid menthyl esters; and c) isolating from the reaction mixture of step b) at least one liquid composition essentially consisting of menthol and menthyl lactate (ML) by vacuum distillation, wherein the weight ratio of menthol to menthyl lactate (ML) in the composition to be subjected to distillation in step c) is in the range of 15:85 to 60:40 wt/wt;

and wherein at least one composition essentially consisting of menthol and a menthyl lactate is obtained, wherein the at least one composition is selected from the group consisting of:

i) a composition having a crystallization point of about +13° C. to +15° C. and having a molar ratio of menthol:menthyl lactate of approximately 75:25;

ii) a composition having a crystallization point of about +2° C. to −1° C. and having a molar ratio of menthol:menthyl lactate of approximately 50:50; and iii) a composition having a crystallization point of about +12° C. to +14° C. and having a molar ratio of menthol:menthyl lactate of approximately 25:75.

14. The method according to claim 11, wherein menthol is L-menthol and/or lactic acid is L-(+)-lactic acid.

* * * * *